US011801058B2

(12) United States Patent
Tieu et al.

(10) Patent No.: US 11,801,058 B2
(45) Date of Patent: Oct. 31, 2023

(54) LIQUID EMBOLIC COMPOSITIONS

(71) Applicant: AccuMedical Beijing Ltd., Beijing (CN)

(72) Inventors: Tai D. Tieu, Fountain Valley, CA (US); Hideo Morita, Irvine, CA (US)

(73) Assignee: AccuMedical Beijing Ltd., Beijing (CN)

( * ) Notice: Subject to any disclaimer, the term of this patent is extended or adjusted under 35 U.S.C. 154(b) by 386 days.

(21) Appl. No.: 17/192,507

(22) Filed: Mar. 4, 2021

(65) Prior Publication Data
US 2022/0280163 A1 Sep. 8, 2022

(51) Int. Cl.
*A61B 17/12* (2006.01)
*A61K 49/04* (2006.01)
*A61L 24/00* (2006.01)
*C08L 29/04* (2006.01)

(52) U.S. Cl.
CPC .. *A61B 17/12113* (2013.01); *A61B 17/12186* (2013.01); *A61K 49/0442* (2013.01); *A61L 24/0015* (2013.01); *C08L 29/04* (2013.01); *A61L 2400/06* (2013.01); *A61L 2430/36* (2013.01)

(58) Field of Classification Search
CPC .............. A61B 17/12; A61B 17/12113; A61B 17/12186; A61F 2/958; A61M 25/10; A61M 25/104
See application file for complete search history.

(56) References Cited

U.S. PATENT DOCUMENTS 5,667,767 A * 9/1997 Greff .................. A61K 49/0414
424/9.4
5,851,508 A 12/1998 Greff et al.
2018/0055516 A1 * 3/2018 Baldwin .......... A61B 17/12181

* cited by examiner

*Primary Examiner* — Vi X Nguyen
(74) *Attorney, Agent, or Firm* — MASTER KEY IP, LLP; Justin G. Sanders

(57) ABSTRACT

The present specification discloses improved liquid embolic compositions, methods of making such liquid embolic compositions, and methods and uses for such liquid embolic compositions.

20 Claims, No Drawings

LIQUID EMBOLIC COMPOSITIONS

RELATED APPLICATIONS

Not applicable.

BACKGROUND

The subject of this patent application relates generally to embolization compositions, and more particularly to improved liquid embolic compositions and associated methods.

Applicant(s) hereby incorporate herein by reference any and all patents and published patent applications cited or referred to in this application.

By way of background, transcatheter embolization ("TE") is a well-established technique in which an occlusive agent is delivered through a catheter to obstruct flow within a targeted blood vessel to prevent or control bleeding. Liquid embolic materials are one type of embolic agent that may be utilized in TE procedures. Liquid embolic materials can include adhesive agents such as acrylates, like n-butyl cyanoacrylate ("n-BCA"), non-adhesive agents such as ethylene vinyl alcohol copolymer ("EVOH"), and cytotoxics such as ethanol. Using non-adhesive liquid embolic agents composed of EVOH copolymer dissolved in a biocompatible solvent such as dimethyl sulfoxide ("DMSO") and mixed with a water insoluble contrast agent such as micronized tantalum powder (in order to monitor injection of the embolic agent into the vascular site and to confirm its presence after the procedure is complete), it is possible to obtain a slower solidification, a more prolonged injection time and a reduced risk of microcatheter entrapment than adhesive liquid embolic agents. However, the relative density of the contrast agents in such known non-adhesive liquid embolic agents requires that the embolic agents be continuously mixed with a shaker machine for a minimum of approximately 20 minutes immediately prior to use, in order to create a suspension of contrast agent that is fluoroscopically visualizable. Thus, for procedures that require multiple vials of such liquid embolic agents, this preparation time for each vial can substantially lengthen the total procedure time. Accordingly, there remains a need for improved liquid embolic agents that require less preparation time and, in turn, reduce the total procedure time for a given procedure. Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY

Aspects of the present invention teach certain benefits in construction and use which give rise to the exemplary advantages described below.

The present invention solves the problems described above by providing improved liquid embolic compositions and associated methods.

Aspects of the present specification disclose a liquid embolic composition. The disclosed liquid embolic composition can comprise a miscible polymer, a radiopaque contrast agent; a biocompatible solvent, and a biocompatible mixing agent that is insoluble in the biocompatible solvent. Other aspects of the present specification disclose a method of making a liquid embolic composition disclosed herein. Other aspects of the present specification disclose a method for embolizing a blood vessel using a liquid embolic composition disclosed herein. The disclosed method comprises the steps of, with the liquid embolic composition positioned within a container, shaking the container by hand, thereby causing the mixing agent to agitate the contrast agent in order to create a suspension of the contrast agent within the liquid embolic composition that is fluoroscopically visualizable; extracting a volume of the liquid embolic composition from the container using a syringe; and introducing the extracted volume of the liquid embolic composition into the blood vessel via the syringe; whereby, with the liquid embolic composition positioned within the blood vessel, a precipitate is formed which embolizes the blood vessel.

Other features and advantages of aspects of the present invention will become apparent from the following more detailed description, taken in conjunction with the accompanying drawings, which illustrate, by way of example, the principles of aspects of the invention.

DETAILED DESCRIPTION

The details of Applicant's improved liquid embolic compositions and associated methods are discussed below. At the outset, however, the following terms will first be defined.

The term "embolic" as used in conjunction with "embolic compositions" and "embolic agents" refers to materials that are injected into a blood vessel which thereafter fill or plug the blood vessel and/or encourages clot formation so that blood flow through the vessel ceases. The embolization of the blood vessel is important in preventing or controlling bleeding (e.g., organ bleeding, gastrointestinal bleeding, vascular bleeding, bleeding associated with an aneurysm) or to ablate diseased tissue (e.g., tumors, etc.) by cutting off its blood supply.

The term "ethylene vinyl alcohol copolymers" (or "EVOH") refers to copolymers comprising residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers used herein are either commercially available or can be prepared by art recognized procedures. In at least one embodiment, the ethylene vinyl alcohol copolymer composition is selected such that a solution of 6 weight percent of the ethylene vinyl alcohol copolymer, 35 weight percent of a contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution (e.g., blood). In at least one embodiment, the copolymers employed herein comprise a mole percent of ethylene of from about 25 to about 60 and a mole percent of vinyl alcohol of from about 40 to about 75. These compositions provide for requisite precipitation rates suitable for use in embolizing blood vessels.

The term "contrast agent" refers to a radiopaque material capable of being monitored during injection into a mammalian subject by, for example, radiography. Such contrast agents include, by way of example only, tantalum, tantalum oxide, barium sulfate, gold, platinum, tungsten, palladium, and iodinated contrast agents such as iopamidol and iohexol, each of which is commercially available in the proper form for in vivo use including a particle size of about 10 µm or less. In still further embodiments, any other contrast agent or particle sizes thereof—now known or later developed—may be substituted so long as the resulting liquid embolic composition is capable of substantially carrying out the functionality described herein.

The term "biocompatible solvent" refers to an organic material liquid at least at body temperature of the mammal in which the ethylene vinyl alcohol copolymer (or other miscible polymer) is soluble and, in the amounts used, is substantially non-toxic. Suitable biocompatible solvents include, by way of example only, dimethyl sulfoxide, homologues of dimethyl sulfoxide, and the like. In still further embodiments, any other biocompatible solvent—now known or later developed—may be substituted so long as the resulting liquid embolic composition is capable of substantially carrying out the functionality described herein.

The term "encapsulation" as used relative to the contrast agent being encapsulated in the precipitate is not meant to infer any physical entrapment of the contrast agent within the precipitate much as a capsule encapsulates a medicament. Rather, this term is used to mean that the contrast agent and copolymer form an integral coherent precipitate which does not separate into a copolymer component and a contrast agent component.

Turning to Applicant's improved liquid embolic compositions, in at least one embodiment, the compositions are prepared by conventional methods whereby each of the components is added and the resulting composition mixed together until the overall composition is substantially homogeneous. Specifically, in at least one such embodiment, sufficient amounts of a miscible polymer (i.e., a polymer that is miscible with the biocompatible solvent) are added to the biocompatible solvent to achieve the effective concentration for the embolic composition. In at least one embodiment, the embolic composition comprises from about 1% to about 20% of the miscible polymer based on a total weight of the embolic composition. In at least one embodiment, the miscible polymer is EVOH. In still further embodiments, any other miscible polymer—now known or later developed—or relative proportion may be substituted so long as the resulting liquid embolic composition is capable of substantially carrying out the functionality described herein. If necessary, in at least one embodiment, gentle heating and stirring can be used to effect dissolution of the miscible polymer into the biocompatible solvent, e.g., 12 hours at 50° C.

In at least one embodiment, sufficient amounts of the contrast agent are added to the biocompatible solvent to achieve the effective concentration for the embolic composition. In at least one embodiment, the embolic composition comprises from about 5% to about 35% of the contrast agent based on the total weight of the embolic composition—though in further embodiments, other relative proportions outside of that range may be substituted, so long as the resulting liquid embolic composition is capable of substantially carrying out the functionality described herein. In at least one embodiment, insofar as the contrast agent is not soluble in the biocompatible solvent, stirring is employed to effect homogeneity of the resulting suspension. In at least one embodiment, in order to enhance formation of the suspension, the particle size of the contrast agent is preferably maintained at about 10 µm or less, and preferably at from about 1 to about 5 µm (e.g., an average size of about 2 µm).

In at least one embodiment, the embolic liquid compositions further comprise a mixing agent configured for lowering a density of the embolic composition and agitating the contrast agent within the embolic composition prior to use of the embolic composition, as discussed further below. In at least one embodiment, the mixing agent is a biocompatible material having a density that is relatively greater than a density of the biocompatible solvent and that is also DMSO insoluble (i.e., the material will not dissolve in dimethyl sulfoxide, analogues/homologues of dimethyl sulfoxide, or the like). Such materials include, by way of example only, polypropylene plastic, polyethylene ("PE"), polyethylene terephthalate ("PET"), polytetrafluoroethylene ("PTFE"), polyether ether ketone ("PEEK"), polyaryletherketone ("PAEK," "PEKK"), and polyetherimide ("PEI"). In at least one embodiment, the mixing agent has a particle size of about 100 nm to about 1 mm, and preferably from about 1,000 nm to about 10,000 nm. Additionally, in at least one embodiment, the particles of the mixing agent each have a substantially spherical shape of substantially uniform diameter. In at least one such embodiment, the particles each have a multifaceted, substantially spherical shape. In at least one alternate embodiment, the particles may each have a substantially asymmetrical, irregular or generally non-spherical shape, such as flakes for example. In still further embodiments, any other biocompatible, DMSO insoluble material and/or particle sizes and shapes thereof—now known or later developed—may be substituted so long as the resulting liquid embolic composition is capable of substantially carrying out the functionality described herein. In at least one embodiment, the mixing agent further comprises a further material having a density that is relatively less than the density of the contrast agent, thereby increasing a buoyancy of the mixing agent by reducing its average density. In at least one such embodiment, the further material consists of a gas entrapped within each particle of the contrast agent or mixing agent or, alternatively, an at least one evacuated void of space within each particle of the contrast agent or mixing agent. In further embodiments, the further material may be any other material (or combination of materials)—now known or later developed—having a density that is relatively less than the density of the contrast agent.

In at least one embodiment, the embolic composition comprises from about 1% to about 40% of the mixing agent based on the total weight of the embolic composition —though in further embodiments, other relative proportions outside of that range may be substituted, so long as the resulting liquid embolic composition is capable of substantially carrying out the functionality described herein. In at least one embodiment, the remaining portion of the embolic composition comprises the biocompatible solvent—i.e., the remaining mass fraction after the EVOH, contrast agent, and mixing agent are accounted for. In at least one such embodiment, the embolic composition comprises from about 5% to about 93% of the biocompatible solvent based on the total weight of the embolic composition—though in further embodiments, other relative proportions outside of that range may be substituted, so long as the resulting liquid embolic composition is capable of substantially carrying out the functionality described herein. In at least one further embodiment, the contrast agent is integrated in the mixing agent.

Thus, in at least one embodiment, an embolic liquid composition disclosed herein comprises from about 1% to about 20% of the miscible polymer, from about 5% to about 35% of the contrast agent, from about 1% to about 40% of the mixing agent; and from about 5% to about 93% of the biocompatible solvent, based on a total weight of the complete liquid embolic composition. In at least one further embodiment, an embolic liquid composition disclosed herein comprises from about 3% to about 10% of the miscible polymer, from about 20% to about 35% of the contrast agent, from about 20% to about 40% of the mixing agent; and from about 15% to about 57% of the biocompatible solvent, based on a total weight of the complete liquid embolic composition.

In at least one embodiment, the particular order of addition of components to the biocompatible solvent is not critical and stirring of the resulting suspension is conducted as necessary to achieve homogeneity of the embolic composition. In at least one embodiment, the mixing/stirring of the composition is conducted under an anhydrous atmosphere at ambient pressure. In at least one embodiment, the resulting embolic composition is heat sterilized and then stored in a suitable container (such as a sealed bottle or vial, for example) until needed.

In at least one embodiment, a liquid embolic composition disclosed herein can be employed in methods for embolizing mammalian blood vessels. Specifically, in at least one embodiment, the container is first shaken by hand for approximately several seconds (such as between 3 to 30 seconds, in at least one embodiment, for example), thereby causing the mixing agent to agitate the contrast agent in order to create a suspension of the contrast agent within the embolic composition that is fluoroscopically visualizable. Once sufficiently shaken, an appropriate amount of the embolic composition is introduced into the selected blood vessel by conventional means (e.g., injection or catheter delivery under fluoroscopy) so that upon precipitation of the EVOH, the blood vessel is embolized. The particular amount of embolic composition employed is dictated by the total volume of the vasculature to be embolized, the concentration of copolymer in the composition, the rate of precipitation (solids formation) of the copolymer, etc. Such factors are well within the skill of the art. The rate of precipitation can be controlled by changing the overall hydrophobicity/hydrophilicity of the copolymer with faster precipitation rates being achieved by a more hydrophobic copolymer composition which, in turn, can be achieved by increasing the ethylene content of the copolymer composition.

In at least one embodiment, a preferred method for delivering a liquid embolic composition disclosed herein to the selected vascular site is via a small diameter medical catheter. The particular catheter employed is not critical, provided that polymeric catheter components are compatible with the embolic composition (i.e., the catheter components will not readily degrade in the embolic composition). In this regard, in at least one such embodiment, it is preferred to use polyethylene in the catheter components because of its inertness in the presence of the embolic composition described herein. Other materials compatible with the embolic compositions, now known or later developed, may be substituted and can be readily determined by one skilled in the art, including, for example, other polyolefins, fluoropolymers (e.g., TEFLON™), silicone, etc.

In at least one embodiment, when the liquid embolic compositions are delivered by catheter, the injection rate dictates, at least in part, the form of the precipitate at the vascular site. Specifically, in at least one such embodiment, low injection rates of approximately 0.05 to 0.3 cc/minute will provide for a precipitate in the form of a kernel or nodule which is particularly beneficial for site specific embolization because the precipitate forms primarily at the point of injection. Contrarily, in at least one such embodiment, high injection rates of about 0.1 to 0.5 or more cc/several seconds (e.g., up to ten seconds) will provide for a filament like mass projecting downstream from the catheter tip, which is particularly beneficial for providing the embolic composition deep into the vascular tree. Such procedures are suitable for embolizing tumor masses, organs and arteriovenous malformations ("AVM").

In at least one embodiment, when the liquid embolic compositions are introduced into the vascular site, the biocompatible solvent diffuses rapidly into the blood and a solid precipitate forms, which precipitate is the EVOH with the contrast agent encapsulated therein. Without being limited to any theory, it is believed that initially, in at least one such embodiment, a soft gel to spongy solid precipitate forms upon contact with the blood, which precipitate is open and fibrous in structure. This precipitate then restricts blood flow, entrapping red cells, thereby causing clot embolization of the blood vessel.

In at least one embodiment, the liquid embolic compositions disclosed herein are useful in embolizing mammalian blood vessels which, in turn, can be used to prevent/control bleeding (e.g., organ bleeding, gastrointestinal bleeding, vascular bleeding, bleeding associated with an aneurysm) or to ablate diseased tissue (e.g., tumors, etc.).

Accordingly, in at least one embodiment, these liquid embolic compositions find use in human and other mammalian subjects requiring embolization of blood vessels.

Additionally, in at least one embodiment, these liquid embolic compositions provide an appropriate vehicle for the delivery of a medicament to the vascular site.

Specifically, a suitable medicament (e.g., a chemotherapeutic agent, growth factor agents, anti-inflammatory agents, anti-spasmatic agents, etc.), which are compatible with the embolic composition, can be included in the embolic composition in therapeutic levels and delivered directly to the vascular site.

From the foregoing description, various modifications and changes in the compositions and methods will occur to those skilled in the art. All such modifications coming within the scope of the appended claims are intended to be included therein.

Aspects of the present specification may also be described as the following embodiments:

1. A liquid embolic composition comprising: from about 1% to about 20% of a miscible polymer; from about 5% to about 35% of a radiopaque contrast agent; from about 5% to about 93% of a biocompatible solvent; and from about 1% to about 40% of a biocompatible mixing agent that is insoluble in the biocompatible solvent; wherein the percent of each of the components is based on a total weight of the complete liquid embolic composition.

2. The liquid embolic composition according to embodiment 1, wherein the composition comprises: from about 3% to about 10% of a miscible polymer; from about 20% to about 35% of a radiopaque contrast agent; from about 15% to about 57% of a biocompatible solvent; and from about 20% to about 40% of a biocompatible mixing agent that is insoluble in the biocompatible solvent; wherein the percent of each of the components is based on a total weight of the complete liquid embolic composition.

3. The liquid embolic composition according to embodiments 1-2, wherein the miscible polymer is an ethylene vinyl alcohol copolymer.

4. The liquid embolic composition according to embodiments 1-3, wherein said ethylene vinyl alcohol copolymer comprises from about 25 to about 60 mole percent of ethylene and from about 40 to about 75 mole percent of vinyl alcohol.

5. The liquid embolic composition according to embodiments 1-4, wherein the contrast agent is at least one of tantalum, tantalum oxide, barium sulfate, gold, platinum, tungsten, palladium, and an iodinated contrast agent.

6. The liquid embolic composition according to embodiments 1-5, wherein the biocompatible solvent is dimethyl sulfoxide or a dimethyl sulfoxide homologue.

7. The liquid embolic composition according to embodiments 1-6, wherein the mixing agent has a density that is relatively greater than a density of the biocompatible solvent.

8. The liquid embolic composition according to embodiments 1-7, wherein the mixing agent is at least one of polypropylene plastic, polyethylene ("PE"), polyethylene terephthalate ("PET"), polytetrafluoroethylene ("PTFE"), polyether ether ketone ("PEEK"), polyaryletherketone ("PAEK," "PEKK"), and polyetherimide ("PEI").

9. The liquid embolic composition according to embodiments 1-8, wherein the mixing agent has a particle size of about 100 nm to about 1 mm.

10. The liquid embolic composition according to embodiments 1-9, wherein the mixing agent has a particle size of about 1,000 nm to about 10,000 nm.

11. The liquid embolic composition according to embodiments 1-10, wherein the mixing agent comprises particles having a substantially spherical shape of substantially uniform diameter.

12. The liquid embolic composition according to embodiments 1-11, wherein the substantially spherical particles of the mixing agent are multifaceted.

13. The liquid embolic composition according to embodiments 1-12, wherein the mixing agent comprises particles having a substantially asymmetrical, irregular or generally non-spherical shape.

14. The liquid embolic composition according to embodiments 1-13, wherein the mixing agent comprises a further material having a density that is relatively less than the density of the contrast agent.

15. The liquid embolic composition according to embodiments 1-14, wherein the further material is an at least one gas entrapped within each particle of the contrast agent or mixing agent.

16. The liquid embolic composition according to embodiments 1-15, wherein each particle of the contrast agent or mixing agent defines an at least one evacuated void of space therewithin, thereby increasing a buoyancy of the contrast agent or mixing agent.

17. The liquid embolic composition according to embodiments 1-16, wherein the contrast agent is integrated in the mixing agent.

18. A liquid embolic composition comprising: from about 1% to about 20% of a miscible polymer; from about 5% to about 35% of a radiopaque contrast agent; from about 5% to about 93% of a biocompatible solvent; and from about 1% to about 40% of a biocompatible mixing agent that is insoluble in the biocompatible solvent and having a density that is relatively greater than a density of the biocompatible solvent, the mixing agent comprising particles having a substantially spherical shape of substantially uniform diameter; wherein the percent of each of the components is based on a total weight of the complete liquid embolic composition.

19. A method for embolizing a blood vessel using the liquid embolic composition of claim 1, the method comprising the steps of: with the liquid embolic composition positioned within a container, shaking the container by hand, thereby causing the mixing agent to agitate the contrast agent in order to create a suspension of the contrast agent within the liquid embolic composition that is fluoroscopically visualizable; extracting a volume of the liquid embolic composition from the container using a syringe; and introducing the extracted volume of the liquid embolic composition into the blood vessel via the syringe; whereby, with the liquid embolic composition positioned within the blood vessel, a precipitate is formed which embolizes the blood vessel.

20. The method according to embodiment 19, wherein the step of shaking the container by hand further comprises the step of shaking the container by hand for a duration of between 3 and 30 seconds.

21. The method according to embodiments 19-20, wherein the step of introducing the extracted volume of the liquid embolic composition into the blood vessel further comprises the step of injecting the extracted volume of embolic composition into the blood vessel at a rate of about 0.05 cc to 0.3 cc per minute.

22. The method according to embodiments 19-21, wherein the step of introducing the extracted volume of the liquid embolic composition into the blood vessel further comprises the step of injecting the extracted volume of embolic composition into the blood vessel at a rate of at least 0.6 cc per minute.

23. The method according to embodiments 19-22, wherein the liquid embolic composition comprises: from about 3% to about 10% of a miscible polymer; from about 20% to about 35% of a radiopaque contrast agent; from about 15% to about 57% of a biocompatible solvent; and from about 20% to about 40% of a biocompatible mixing agent that is insoluble in the biocompatible solvent; wherein the percent of each of the components is based on a total weight of the complete liquid embolic composition.

24. The method according to embodiments 19-23, wherein the miscible polymer is an ethylene vinyl alcohol copolymer.

25. The method according to embodiments 19-24, wherein said ethylene vinyl alcohol copolymer comprises from about 25 to about 60 mole percent of ethylene and from about 40 to about 75 mole percent of vinyl alcohol.

26. The method according to embodiments 19-25, wherein the contrast agent is at least one of tantalum, tantalum oxide, barium sulfate, gold, platinum, tungsten, palladium, and an iodinated contrast agent.

27. The method according to embodiments 19-26, wherein the biocompatible solvent is dimethyl sulfoxide or a dimethyl sulfoxide homologue.
28. The method according to embodiments 19-27, wherein the mixing agent has a density that is relatively greater than a density of the biocompatible solvent.
29. The method according to embodiments 19-28, wherein the mixing agent is at least one of polypropylene plastic, polyethylene ("PE"), polyethylene terephthalate ("PET"), polytetrafluoroethylene ("PTFE"), polyether ether ketone ("PEEK"), polyaryletherketone ("PAEK," "PEKK"), and polyetherimide ("PEI").
30. The method according to embodiments 19-29, wherein the mixing agent has a particle size of about 100 nm to about 1 mm.
31. The method according to embodiments 19-30, wherein the mixing agent has a particle size of about 1,000 nm to about 10,000 nm.
32. The method according to embodiments 19-31, wherein the mixing agent comprises particles having a substantially spherical shape of substantially uniform diameter.
33. The method according to embodiments 19-32, wherein the substantially spherical particles of the mixing agent are multifaceted.
34. The method according to embodiments 19-33, wherein the mixing agent comprises particles having a substantially asymmetrical, irregular or generally non-spherical shape.
35. The method according to embodiments 19-34, wherein the mixing agent comprises a further material having a density that is relatively less than the density of the contrast agent.
36. The method according to embodiments 19-35, wherein the further material is an at least one gas entrapped within each particle of the contrast agent or mixing agent.
37. The method according to embodiments 19-36, wherein each particle of the contrast agent or mixing agent defines an at least one evacuated void of space therewithin, thereby increasing a buoyancy of the contrast agent or mixing agent.
38. The method according to embodiments 19-37, wherein the contrast agent is integrated in the mixing agent.

In closing, regarding the exemplary embodiments of the present invention as described herein, it will be appreciated that improved liquid embolic compositions and associated methods are disclosed. Because the principles of the invention may be practiced in a number of configurations beyond those shown and described, it is to be understood that the invention is not in any way limited by the exemplary embodiments, but is generally directed to improved liquid embolic compositions and associated methods and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc. — for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

It should be understood that the methods, and the order in which the respective elements of each method are performed, are purely exemplary. Depending on the implementation, they may be performed in any order or in parallel, unless indicated otherwise in the present disclosure.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A liquid embolic composition comprising:
   from about 1% to about 20% of a miscible polymer;
   from about 5% to about 35% of a radiopaque contrast agent;
   from about 5% to about 93% of a biocompatible solvent; and
   from about 1% to about 40% of a biocompatible mixing agent that is insoluble in the biocompatible solvent;
   wherein the percent of each of the components is based on a total weight of the complete liquid embolic composition.

2. The liquid embolic composition of claim 1, wherein the composition comprises:
   from about 3% to about 10% of a miscible polymer;
   from about 20% to about 35% of a radiopaque contrast agent;
   from about 15% to about 57% of a biocompatible solvent; and
   from about 20% to about 40% of a biocompatible mixing agent that is insoluble in the biocompatible solvent;
   wherein the percent of each of the components is based on a total weight of the complete liquid embolic composition.

3. The liquid embolic composition of claim 1, wherein the miscible polymer is an ethylene vinyl alcohol copolymer.

4. The liquid embolic composition of claim 1, wherein the contrast agent is at least one of tantalum, tantalum oxide, barium sulfate, gold, platinum, tungsten, palladium, and an iodinated contrast agent.

5. The liquid embolic composition of claim 1, wherein the biocompatible solvent is dimethyl sulfoxide or a dimethyl sulfoxide homologue.

6. The liquid embolic composition of claim 1, wherein the mixing agent has a density that is relatively greater than a density of the biocompatible solvent.

7. The liquid embolic composition of claim 6, wherein the mixing agent is at least one of polypropylene plastic, polyethylene ("PE"), polyethylene terephthalate ("PET"), polytetrafluoroethylene ("PTFE"), polyether ether ketone ("PEEK"), polyaryletherketone ("PAEK," "PEKK"), and polyetherimide ("PEI").

8. The liquid embolic composition of claim 7, wherein the mixing agent has a particle size of about 100 nm to about 1 mm.

9. The liquid embolic composition of claim 8, wherein the mixing agent has a particle size of about 1,000 nm to about 10,000 nm.

10. The liquid embolic composition of claim 8, wherein the mixing agent comprises particles having a substantially spherical shape of substantially uniform diameter.

11. The liquid embolic composition of claim 10, wherein the substantially spherical particles of the mixing agent are multifaceted.

12. The liquid embolic composition of claim 1, wherein the mixing agent comprises a further material having a density that is relatively less than the density of the contrast agent.

13. The liquid embolic composition of claim 12, wherein the further material is an at least one gas entrapped within each particle of the contrast agent or mixing agent.

14. The liquid embolic composition of claim 1, wherein each particle of the contrast agent or mixing agent defines an at least one evacuated void of space therewithin, thereby increasing a buoyancy of the contrast agent or mixing agent.

15. The liquid embolic composition of claim 1, wherein the contrast agent is integrated in the mixing agent.

16. A method for embolizing a blood vessel using the liquid embolic composition of claim 1, the method comprising the steps of:

with the liquid embolic composition positioned within a container, shaking the container by hand, thereby causing the mixing agent to agitate the contrast agent in order to create a suspension of the contrast agent within the liquid embolic composition that is fluoroscopically visualizable;

extracting a volume of the liquid embolic composition from the container using a syringe; and introducing the extracted volume of the liquid embolic composition into the blood vessel via the syringe;

whereby, with the liquid embolic composition positioned within the blood vessel, a precipitate is formed which embolizes the blood vessel.

17. The method of claim 16, wherein the step of shaking the container by hand further comprises the step of shaking the container by hand for a duration of between 3 and 30 seconds.

18. The method of claim 16, wherein the step of introducing the extracted volume of the liquid embolic composition into the blood vessel further comprises the step of injecting the extracted volume of embolic composition into the blood vessel at a rate of about 0.05 cc to 0.3 cc per minute.

19. The method of claim 16, wherein the step of introducing the extracted volume of the liquid embolic composition into the blood vessel further comprises the step of injecting the extracted volume of embolic composition into the blood vessel at a rate of at least 0.6 cc per minute.

20. A liquid embolic composition comprising:
from about 1% to about 20% of a miscible polymer;
from about 5% to about 35% of a radiopaque contrast agent;
from about 5% to about 93% of a biocompatible solvent; and
from about 1% to about 40% of a biocompatible mixing agent that is insoluble in the biocompatible solvent and having a density that is relatively greater than a density of the biocompatible solvent, the mixing agent comprising particles having a substantially spherical shape of substantially uniform diameter;
wherein the percent of each of the components is based on a total weight of the complete liquid embolic composition.

* * * * *